US012734178B2

(12) United States Patent
Xu et al.

(10) Patent No.: US 12,734,178 B2
(45) Date of Patent: Sep. 15, 2026

(54) PREPARATION FOR ETHINYLESTRADIOL-CYCLODEXTRIN COMPLEX AND USE THEREOF

(71) Applicant: NATIONAL RESEARCH INSTITUTE FOR FAMILY PLANNING, Beijing (CN)

(72) Inventors: Juan Xu, Beijing (CN); Lifeng Ning, Beijing (CN); Bin He, Beijing (CN)

(73) Assignee: NATIONAL RESEARCH INSTITUTE FOR FAMILY PLANNING, Beijing (CN)

( * ) Notice: Subject to any disclaimer, the term of this patent is extended or adjusted under 35 U.S.C. 154(b) by 468 days.

(21) Appl. No.: 18/555,321

(22) PCT Filed: Jan. 18, 2023

(86) PCT No.: PCT/CN2023/072891
§ 371 (c)(1),
(2) Date: Oct. 13, 2023

(87) PCT Pub. No.: WO2023/143306
PCT Pub. Date: Aug. 3, 2023

(65) Prior Publication Data

US 2024/0189323 A1 Jun. 13, 2024

(30) Foreign Application Priority Data

Jan. 29, 2022 (CN) ........................ 202210112575.7

(51) Int. Cl.
*A61K 9/16* (2006.01)
*A61K 31/567* (2006.01)

(52) U.S. Cl.
CPC .......... *A61K 31/567* (2013.01); *A61K 9/1652* (2013.01)

(58) Field of Classification Search
CPC ........................... A61K 31/567; A61K 9/1652
See application file for complete search history.

(56) References Cited

U.S. PATENT DOCUMENTS 5,798,338 A 8/1998 Backensfeld et al.

FOREIGN PATENT DOCUMENTS

| | | | | |
|---|---|---|---|---|
| CN | 1482921 A | | 3/2004 | |
| CN | 104013972 A | | 9/2014 | |
| CN | 114225050 A | | 3/2022 | |
| WO | WO 2007085498 | * | 8/2007 | .............. A61K 9/00 |
| WO | 2020120548 A1 | | 6/2020 | |

OTHER PUBLICATIONS

Gao, Yanling; "Non-official translation: Study on Solubilization of Modified cyclodextrin"; West Leather; vol. 1671-1602, Oct. 31, 2017; pp. 3.

* cited by examiner

*Primary Examiner* — Erich A Leeser
(74) *Attorney, Agent, or Firm* — NKL Law; Allen Xue

(57) ABSTRACT

Disclosed are preparation for an ethinylestradiol-cyclodextrin complex and use thereof. The ethinylestradiol-cyclodextrin complex utilizes the properties of cyclodextrin that the inner cavity is hydrophobic and the outer surface is hydrophilic to increase the water solubility of the ethinylestradiol-cyclodextrin complex that is also an ethinylestradiol drug, so that the solubility of ethinylestradiol is greatly increased and the bioavailability of water-insoluble ethinylestradiol is improved, thereby providing the possibility for changing the administration mode and homogeneous injection of ethinylestradiol.

20 Claims, 8 Drawing Sheets

6a 6b 6c 6e 6f 6g

PREPARATION FOR ETHINYLESTRADIOL-CYCLODEXTRIN COMPLEX AND USE THEREOF

CROSS-REFERENCE TO RELATED APPLICATIONS

The present application is a U.S. national stage entry of PCT international application no. PCT/CN2023/072891, filed on Jan. 18, 2023, which claims priority to the Chinese Patent Application No. 2022101125757 entitled "PREPARATION FOR ETHINYLESTRADIOL-CYCLODEXTRIN COMPLEX AND USE THEREOF" and filed with the China National Intellectual Property Administration on Jan. 29, 2022, the content of each is incorporated herein by reference in its entirety.

TECHNICAL FIELD

The present application relates to the field of biology, and relates to preparation for an ethinylestradiol-cyclodextrin complex and use thereof.

BACKGROUND

Ethinylestradiol is a potent oral estrogen drug, which has the chemical name of 3-hydroxy-19-nor-17α-pregna-1,3,5(10)-trien-20-yn-17-ol, the molecular formula of $C_{20}H_{24}O_2$, and the molecular weight of 296.4. Ethinylestradiol is a white or milk-white crystalline powder. Ethinylestradiol is soluble in acetone, methanol, ethanol, propanol, ethyl ether, chloroform, dioxane, vegetable oil, and a sodium hydroxide solution, is almost insoluble in water, and has no smell. Ethinylestradiol can be used for supplementing estrogen deficiency and treating female sexual gland dysfunction, amenorrhea, climacteric syndrome, advanced breast cancer (postmenopausal women), advanced prostate cancer, infantile cryptorchidism, androgen excess, a pituitary tumor, etc. Ethinylestradiol can inhibit ovulation when used together with a progestogen drug, and can be used as a contraceptive.

Poor water solubility is a common problem for steroid compounds, and the bioavailability of a drug is directly proportional to the water solubility of the drug. At present, for the solubilization of estrogen drugs, the solubilization of progesterone drugs is the most common, wherein β-cyclodextrin or hydroxypropyl-β-cyclodextrin is mainly used as a host molecule to prepare a host-guest clathrate, and use of cyclodextrin for increasing the solubility of progesterone has not been reported. The problems to be solved at present are to improve the water solubility and bioavailability of ethinylestradiol drugs, increase the stability of ethinylestradiol drugs and reduce oral dosage.

SUMMARY

The technical problem to be solved by the present disclosure is to provide a cyclodextrin/ethinylestradiol complex aiming at solving the existing problems that ethinylestradiol is poor in solubility, unstable and incapable of well playing the efficacy and the like. The present disclosure aims at improving the water solubility of a hydrophobic drug ethinylestradiol so as to improve the bioavailability of a ethinylestradiol drug.

In order to achieve the objects above, the present disclosure specifically adopts the following technical solutions:

A first aspect of the present disclosure provides a pharmaceutical composition, comprising ethinylestradiol and cyclodextrin.

In some embodiments, the ethinylestradiol and the cyclodextrin interact to form a clathrate.

In some embodiments, the cyclodextrin is selected from β-cyclodextrin or a derivative thereof.

In some embodiments, the β-cyclodextrin derivative is selected from ethylenediamine-β-cyclodextrin, diethylenetriamine-β-cyclodextrin, triethylenetetramine-β-cyclodextrin, tetraethylenepentamine-β-cyclodextrin, and hydroxypropyl-β-cyclodextrin.

In some embodiments, the β-cyclodextrin derivative is selected from diethylenetriamine-β-cyclodextrin.

In some embodiments, the cyclodextrin and the ethinylestradiol have a stoichiometric ratio of 1:1.

In some embodiments, the method by which the ethinylestradiol and the cyclodextrin interact to form a clathrate is as follows:

dissolving the cyclodextrin in deionized water, adding the ethinylestradiol and a co-solvent, heating and stirring the mixture; then continuously stirring the mixture at room temperature and keeping the mixture overnight at low temperature; filtering the mixture, and drying to give a white solid powder.

In some embodiments, the mixture is continuously stirred at room temperature and kept at 4° C. overnight.

In some embodiments, the heating temperature is 40° C.

In some embodiments, the co-solvent is ethanol.

In some embodiments, the drying is freeze drying.

In a specific embodiment, the method by which the ethinylestradiol and the cyclodextrin interact to form a clathrate is as follows: dissolving the cyclodextrin in 10 mL of 40° C. deionized water, adding 0.085 g of ethinylestradiol and 1 mL of an ethanol co-solvent, and stirring the mixture at 40° C. for 1 h; then stopping the heating, continuously stirring the mixture for 3 h at room temperature, and placing the mixture in a refrigerator at 4° C. overnight; filtering the solution described above after 12 h, and freeze-drying the filtrate for 12 h to give a white solid powder of diethylenetriamine-β-cyclodextrin/ethinylestradiol complex.

In some embodiments, the pharmaceutical composition further comprises a pharmaceutically acceptable carrier.

A second aspect of the present disclosure provides a preparation method for a cyclodextrin/ethinylestradiol complex, wherein the preparation method is as follows:

dissolving the cyclodextrin in deionized water, adding the ethinylestradiol and a co-solvent, heating and stirring the mixture; then continuously stirring the mixture at room temperature and keeping the mixture overnight at low temperature; filtering the mixture, and drying to give a white solid powder.

In some embodiments, the mixture is continuously stirred at room temperature and kept at 4° C. overnight. In some embodiments, the heating temperature is 40° C.

In some embodiments, the co-solvent is ethanol.

In some embodiments, the drying is freeze drying.

In some embodiments, the cyclodextrin is selected from β-cyclodextrin or a derivative thereof.

In some embodiments, the β-cyclodextrin derivative is selected from ethylenediamine-β-cyclodextrin, diethylenetriamine-β-cyclodextrin, triethylenetetramine-β-cyclodextrin, tetraethylenepentamine-β-cyclodextrin, and hydroxypropyl-β-cyclodextrin.

In some embodiments, the β-cyclodextrin derivative is selected from diethylenetriamine-β-cyclodextrin.

In some embodiments, a preparation method for the diethylenetriamine-β-cyclodextrin is as follows:

1) dissolving β-cyclodextrin in a sodium hydroxide solution to give an alkaline β-cyclodextrin solution;
2) dissolving toluenesulfonyl chloride in acetonitrile, adding the mixture to the alkaline β-cyclodextrin solution described above, adjusting the pH to give a suspension, obtaining a precipitate at low temperature, and drying to give 6-p-toluenesulfonyl-β-cyclodextrin;
3) dissolving the 6-p-toluenesulfonyl-β-cyclodextrin in N-methylpyrrolidone, heating, adding potassium iodide and diethylenetriamine, stirring the mixture at high temperature under nitrogen atmosphere, then cooling to room temperature, collecting a precipitate, and drying to give the diethylenetriamine-β-cyclodextrin.

In some embodiments, the pH is adjusted to 5-7 with hydrochloric acid in 2).

In some embodiments, the suspension in 2) is at 4° C. overnight to give a precipitate.

In some embodiments, the precipitate in 2) is washed with ethanol.

In some embodiments, the drying is at 50° C. to give 6-p-toluenesulfonyl-β-cyclodextrin in 2).

In some embodiments, the mixture is stirred at 70° ° C. under nitrogen atmosphere in 3).

In some embodiments, the mixture in 3) is stirred at 70° ° C. for 7 h under nitrogen atmosphere.

In some embodiments, the precipitate is collected using suction filtration in 3).

In some embodiments, the precipitate in 3) is dried under vacuum at 50° C.

In a specific embodiment, a preparation method for the diethylenetriamine-β-cyclodextrin is as follows:

dissolving recrystallized β-cyclodextrin in a sodium hydroxide aqueous solution, and stirring for about 30 min to give an alkaline β-cyclodextrin solution; then dissolving p-toluenesulfonyl chloride in acetonitrile, dropwise adding the mixture to the β-cyclodextrin solution described above; stirring at room temperature for 2.0 h, adjusting the pH of the solution to 5-7 with hydrochloric acid, and freezing the obtained suspension at 4° C. overnight to ensure complete precipitation; then filtering to collect a white precipitate, and washing the precipitate with a large amount of an ethanol solution; drying all the obtained precipitates at 50° C. for 12 h to give a pure white solid of 6-p-toluenesulfonyl-β-cyclodextrin; dissolving the 6-p-toluenesulfonyl-β-cyclodextrin in N-methylpyrrolidone, heating to 70° C., then adding potassium iodide and diethylenetriamine, and stirring the mixture at 70° C. under nitrogen atmosphere for 7 h; cooling the obtained light yellow solution to room temperature, washing the solution with ethanol, separating and collecting a white precipitate using suction filtration, and drying the obtained solid under vacuum at 50° C. for 12 h to give a white solid powder of diethylenetriamine-β-cyclodextrin.

In some embodiments, the solubility of the diethylenetriamine-β-cyclodextrin can reach 600 g/L.

A third aspect of the present disclosure provides a method for increasing the solubility of ethinylestradiol and improving the release performance of the ethinylestradiol, wherein the ethinylestradiol is included by cyclodextrin.

In some embodiments, the cyclodextrin is selected from β-cyclodextrin or a derivative thereof.

In some embodiments, the β-cyclodextrin derivative is selected from ethylenediamine-β-cyclodextrin, diethylenetriamine-β-cyclodextrin, triethylenetetramine-β-cyclodextrin, tetraethylenepentamine-β-cyclodextrin, and hydroxypropyl-β-cyclodextrin.

In some embodiments, the β-cyclodextrin derivative is selected from diethylenetriamine-β-cyclodextrin.

In some embodiments, the method for including ethinylestradiol with cyclodextrin is as follows: dissolving the cyclodextrin in deionized water, adding the ethinylestradiol and a co-solvent, heating and stirring the mixture; then continuously stirring the mixture at room temperature and keeping the mixture overnight at low temperature; filtering the mixture, and drying to give a white solid powder. In some embodiments, the mixture is continuously stirred at room temperature and kept at 4° C. overnight.

In some embodiments, the heating temperature is 40° C.

In some embodiments, the co-solvent is ethanol.

In some embodiments, the drying is freeze drying.

A fourth aspect of the present disclosure provides a method for contraception or for treating a gynecological disease, comprising administering to a subject in need thereof an effective amount of the pharmaceutical composition according to the first aspect. In some embodiments, the subject is a mammal.

In some embodiments, the mammal includes a human, a non-human primate, a rabbit, a sheep, a rat, a dog, a cat, a pig, or a mouse.

As a preferred embodiment of the present disclosure, the subject is a human.

In the present disclosure, the gynecological disease includes, but is not limited to, menstrual disorders, dysmenorrhea, endometriosis, premenstrual syndrome, breast pain, menopausal syndrome, and endometrial cancer. The gynecological disease also includes a gynecological disease with a cardiovascular and cerebrovascular disease. The cardiovascular and cerebrovascular disease includes ischemic stroke, stabbing pain in chest and hypochondrium, bruises and swelling, headache, hypertension, coronary atherosclerotic heart disease (coronary heart disease), migraine, ischemic encephalopathy, and brain injury.

In the present disclosure, “clathrate” and “complex” are used interchangeably.

In the present disclosure, the term “pharmaceutically acceptable carrier” generally refers to a pharmaceutically acceptable composition, such as a liquid or solid filler, diluent, excipient, manufacturing aid (e.g., a lubricant, talc magnesium, calcium stearate or zinc stearate, or stearic acid), or solvent encapsulating material for introducing an active agent into the body. Each carrier must be “acceptable” in the sense of being compatible with the other ingredients of the formulation and not injurious to the patient. Examples of suitable aqueous and non-aqueous carriers that can be used in the pharmaceutical composition of the present disclosure include, for example, water, ethanol, polyols (such as glycerol, propylene glycol, polyethylene glycol, and the like), vegetable oils (such as olive oil), and injectable organic esters (such as ethyl oleate), and suitable mixtures thereof. Proper fluidity may be maintained, for example, by use of a coating material, such as lecithin, and in the case of dispersion, by the maintenance of the required particle size and by use of a surfactant.

Various adjuvants, such as a wetting agent, an emulsifying agent, a lubricant (e.g., sodium lauryl sulfate and magnesium stearate), a coloring agent, an isolating agent, a coating agent, a sweetening agent, a flavoring agent, a preservative and an antioxidant, may also be included in the pharmaceutical composition. Some examples of pharmaceutically acceptable antioxidants include: (1) water-soluble antioxidants, such as ascorbic acid, cysteine hydrochloride, sodium bisulfate, sodium metabisulfite and sodium sulfite; (2) oil-soluble antioxidants, such as ascorbyl palmitate, butylated hydroxyanisole (BHA), butylated hydroxytoluene (BHT), lecithin, propyl gallate and a tocopherol; and (3) metal chelating agents, such as citric acid, ethylenediamine tetraacetic acid (EDTA), sorbitol, tartaric acid and phosphoric acid. In some embodiments, the pharmaceutical formulation comprises an excipient selected from, for example, cellulose, a liposome, a micelle-forming agent (e.g., bile acid), and a polymeric carrier (e.g., polyesters and polyanhydrides). Suspensions, in addition to the active compound, may contain a suspending agent, for example, ethoxylated isostearyl alcohol, polyoxyethylene sorbitol and sorbitan esters, microcrystalline cellulose, aluminum metahydroxide, bentonite, agar and tragacanth, and mixtures thereof. Prevention of the action of microorganisms on the active compound can be ensured by the incorporation of various antibacterial and antifungal agents, for example, parabens, chlorobutanol, phenol, sorbic acid, and the like. It may also be desirable to include an isotonic agent, such as sugars, sodium chloride, and the like in the composition.

The formulation of the present disclosure suitable for oral administration may be in the form of a capsule, a cachet, a pill, a tablet, a lozenge (using a flavoring agent, typically sucrose and acacia or tragacanth), a powder, or a granule, or as a solution or suspension in an aqueous or non-aqueous liquid, or as an oil-in-water or water-in-oil liquid emulsion, or as an elixir or syrup, or as a pastille (using an inert matrix, such as gelatin and glycerol, or sucrose and acacia) and/or as mouthwash, and the like, each form containing a predetermined amount of the clathrate or the complex of the present disclosure as the active ingredient. The pharmaceutical composition may also be administered in the form of a bolus, an electuary or a paste.

Methods for preparing the formulation or the composition generally include the step of blending the clathrate or the complex of the present disclosure with a carrier and optionally one or more adjuvants. For solid dosage forms (e.g., a capsule, a tablet, a pill, a powder, a granule, a buccal tablet, etc.), the active compound may be blended with a finely divided solid carrier and usually shaped, such as by pelleting, tabletting, granulating, powdering or coating. Typically, the solid carrier may include, for example, sodium citrate or dicalcium phosphate, and/or any one of the following: (1) fillers or extenders, such as starch, lactose, sucrose, glucose, mannitol, and/or silicic acid; (2) binders, such as carboxymethyl cellulose, alginate, gelatin, polyvinylpyrrolidone, sucrose and/or acacia; (3) humectants, such as glycerol; (4) disintegrants, such as agar, calcium carbonate, potato or tapioca starch, alginic acid, certain silicates, and sodium carbonate; (5) solution retarders, such as paraffin; (6) absorption enhancers, such as quaternary ammonium compounds and surfactants, such as poloxamer and sodium lauryl sulfate; (7) wetting agents, such as, for example, cetyl alcohol, glycerol monostearate and nonionic surfactants; (8) absorbents, such as kaolin and bentonite; (9) lubricants, such as talc, calcium stearate, magnesium stearate, solid polyethylene glycol, sodium lauryl sulfate, zinc stearate, sodium stearate, stearic acid and mixtures thereof; (10) coloring agents; and (11) controlled-release agents, such as crospovidone or ethyl cellulose. In the case of capsules, tablets, and pills, the pharmaceutical composition may further comprise buffers. The solid composition of a similar type may also be employed as fillers in gelatin capsules with soft and hard shells using an excipient such as lactose or milk sugar as well as high-molecular-weight polyethylene glycol, and the like.

The tablet may be prepared by compression or molding, optionally with one or more additional ingredients. Compressed tablets may be prepared using a binder (for example, gelatin or hydroxypropylmethyl cellulose), a lubricant, an inert diluent, a preservative, a disintegrant (for example, sodium starch glycolate or croscarmellose sodium), a surfactant, or a dispersant.

Other solid dosage forms of tablets and active agents, such as a capsule, a pill, and a granule, may optionally be scored or prepared using a coating and a shell, such as an enteric coating and other coatings well known in the pharmaceutical formulation art. The dosage form may also be formulated to provide sustained or controlled release of the active ingredient therein using, for example, hydroxypropylmethyl cellulose in varying proportions (to provide the desired release profile), other polymer matrices, liposomes and/or microspheres. Alternatively, the dosage form may be formulated for rapid release, e.g., freeze drying.

Typically, the dosage form must be sterile. To this end, the dosage form may be sterilized, for example, by filtration through a bacteria-retaining filter, or by incorporating sterilizing agents in the form of a sterile solid composition which may be dissolved in sterile water or some other sterile injection mediums prior to use.

The liquid dosage form is typically a pharmaceutically acceptable emulsion, microemulsion, solution, suspension, syrup or elixir of the active agent. In addition to the active ingredient, the liquid dosage form may comprise an inert diluent commonly used in the art such as, for example, water or other solvents, solubilizers and emulsifiers, such as ethyl alcohol, isopropanol, ethyl carbonate, ethyl acetate, benzyl alcohol, benzyl benzoate, propylene glycol, 1,3-butanediol, oils (in particular, cottonseed oil, peanut oil, corn oil, germ oil, olive oil, castor oil, and sesame oil), glycerol, tetrahydrofurfuryl alcohol, polyethylene glycol and fatty acid esters of sorbitan, and mixtures thereof. The dosage form particularly for topical or transdermal administration may be in the form of, for example, a powder, a spray, an ointment, a paste, a cream, a lotions, a gel, a solution, or a patch. The active compound may be mixed under sterile conditions with a pharmaceutically acceptable carrier, and with any preservatives, buffers, or propellants which may be necessary. In addition to the clathrate of the present disclosure, the topical or transdermal dosage form may further comprise one or more excipients, such as the excipients selected from animal and vegetable fats, oils, waxes, paraffins, starch, tragacanth, cellulose derivatives, polyethylene glycol, organic silicon, bentonite, silicic acid, talc and zinc oxide, and mixtures thereof. The spray may further comprise a conventional propellant, such as chlorofluorocarbons and volatile unsubstituted hydrocarbons (such as butane or propane).

Advantages and beneficial effects of the described examples:

The cyclodextrin/ethinylestradiol complex, particularly the diethylenetriamine-β-cyclodextrin/ethinylestradiol complex, is prepared for the first time. The solubility of ethinylestradiol can be improved by about 100 times, so that the bioavailability of the water-insoluble drug ethinylestradiol is improved, and the possibility is provided for changing the route of administration of ethinylestradiol and for homogeneous injection of ethinylestradiol.

β-Cyclodextrin is modified using an amine molecule to give a cyclodextrin derivative with better water solubility and lower price as a host molecule for inclusion, so that the solubility of β-cyclodextrin is increased, and the binding sites of β-cyclodextrin and ethinylestradiol are increased.

DETAILED DESCRIPTION

Figure 1:
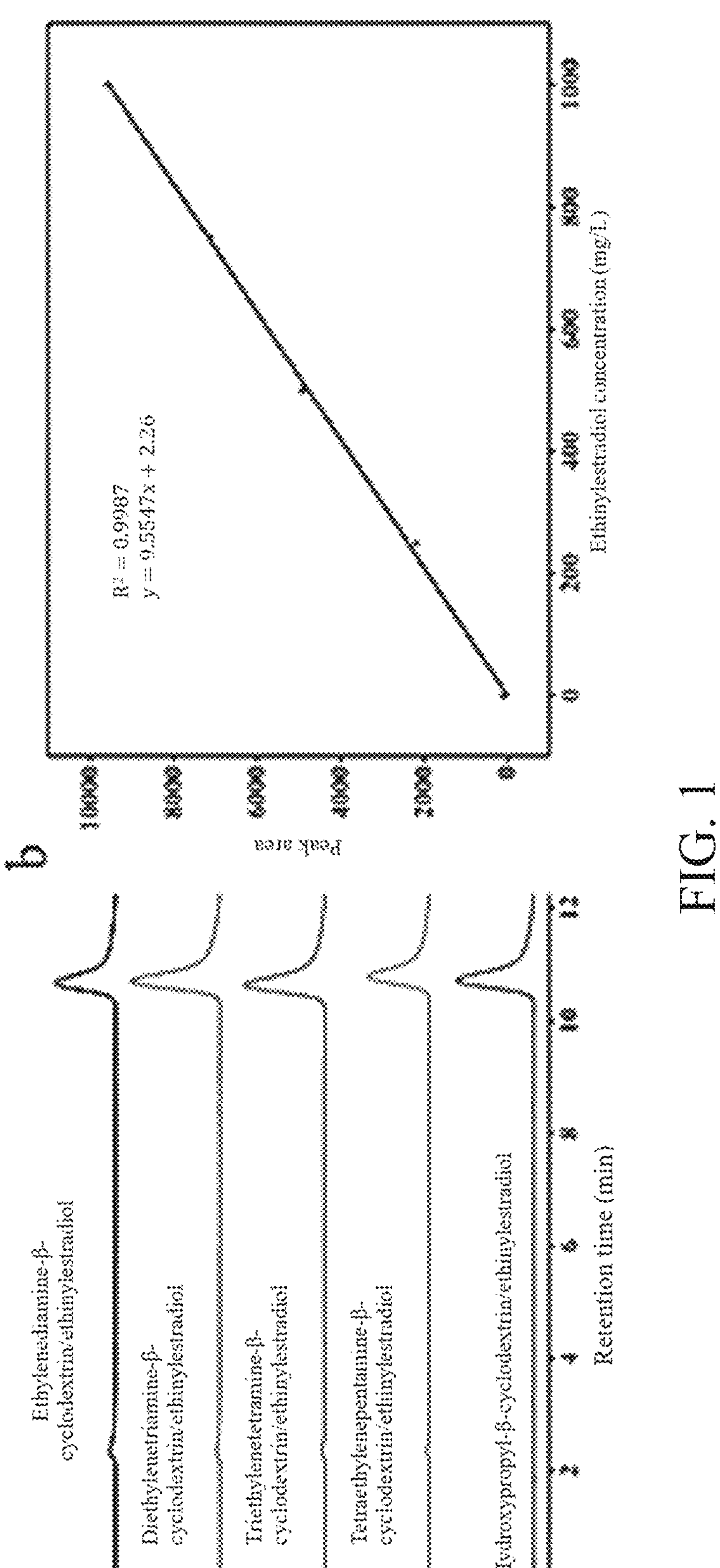
FIG. 1 is a graph showing the detection of the inclusion capacity of different host molecules, wherein 1*a* is a liquid chromatogram of different β-cyclodextrin derivative/ethinylestradiol complexes, 1*b* is a standard curve of ethinylestradiol, 1*c* is the ethinylestradiol peak areas in different β-cyclodextrin derivative/ethinylestradiol complexes, and 1*d* is the ethinylestradiol concentrations in different β-cyclodextrin derivative/ethinylestradiol complexes.
Figure 1:
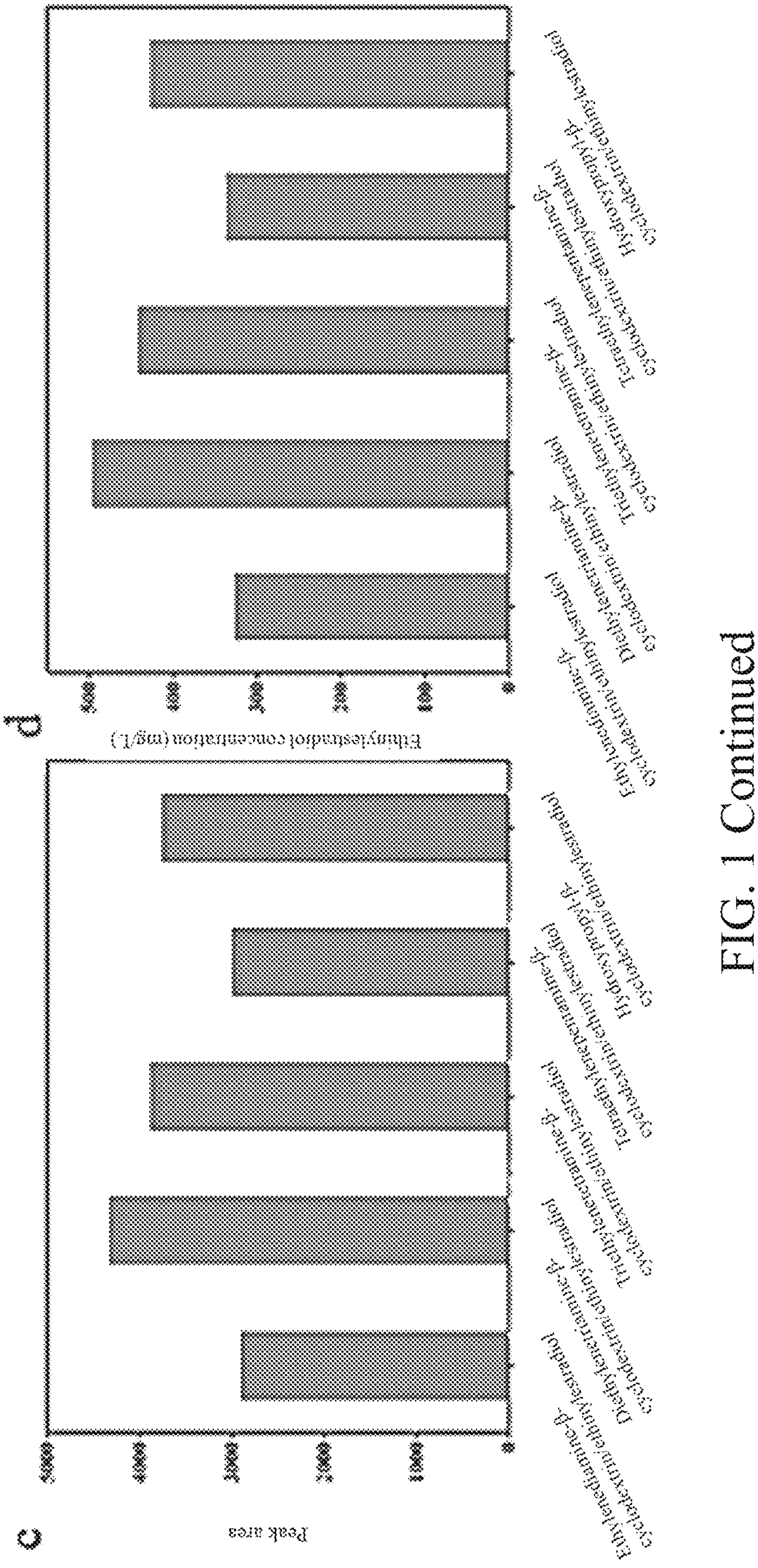

The present invention will be further illustrated with reference to the following specific examples, which are illustrative only and are not to be construed as limiting the present invention. It can be understood by those of ordinary skill in the art that various changes, modifications, replacements and variations can be made to these examples without departing from the principle and purpose of the present invention, and the scope of the present invention is defined by the claims and equivalents thereof. Experimental procedures without specified conditions in the following examples, are generally carried out under conventional conditions, or under conditions recommended by the manufacturer.

Example: Preparation of Cyclodextrin/Ethinylestradiol Complex and Functional Detection I. Materials β-Cyclodextrin was purchased from Zibo Qianhui Biotechnology Co., Ltd. Diethylenetriamine and p-toluenesulfonyl chloride (99%) were purchased from Aladdin (Shanghai, China). Sodium hydroxide, N-methylpyrrolidone, and acetonitrile were provided by Tianjin Kemiou Chemical Reagent Co., Ltd., China. Potassium iodide was purchased from Tianjin Hengxing Chemical Reagent Manufacturing Co., Ltd. Ultrapure water of Millipore, USA and chromatographic grade methanol of Tianjin Fuyu Fine Chemical Co., Ltd. were used in the chromatographic research. All other reagents and solvents were analytical grade and used as required for safety without further purification.

B. Method

1. Preparation of Diethylenetriamine-β-Cyclodextrin/Ethinylestradiol

1) Preparation of Diethylenetriamine-β-Cyclodextrin 0.054 mol of recrystallized β-cyclodextrin was dissolved in an 8.4 mol/L sodium hydroxide aqueous solution, and the mixture was stirred for about 30 min to give an alkaline β-cyclodextrin solution. Then 0.058 mol of p-toluenesulfonyl chloride was dissolved in 30 mL of acetonitrile, and the mixture was dropwise added to the β-cyclodextrin solution described above. The mixture was stirred at room temperature for 2.0 h, the pH of the solution was adjusted to 5-7 with hydrochloric acid, and the obtained suspension was frozen at 4° C. overnight to ensure complete precipitation. Then the suspension was filtered and a white precipitate was collected, and the precipitate was washed with a large amount of an ethanol solution. All the obtained precipitates were dried at 50° C. for 12 h to give 9.2 g of a pure white solid of 6-p-toluenesulfonyl-β-cyclodextrin. $1.59\times10^{-3}$ mol of the 6-p-toluenesulfonyl-β-cyclodextrin was dissolved in 5 mL of N-methylpyrrolidone, the mixture was heated to 70° C., then 0.025 g of potassium iodide and 0.73 g of diethylenetriamine were added, and the mixture was stirred at 70° C. under nitrogen atmosphere for 7 h. The obtained light yellow solution was cooled to room temperature and washed with 100 mL of ethanol. A white precipitate was separated and collected using suction filtration, and the obtained solid was dried under vacuum at 50° C. for 12 h to give a white solid powder of diethylenetriamine-β-cyclodextrin, the solubility of which can reach 600 g/L.

2) Preparation of Diethylenetriamine-β-Cyclodextrin/Ethinylestradiol Complex

Diethylenetriamine-β-cyclodextrin was dissolved in 10 mL of 40° C. deionized water, 0.085 g of ethinylestradiol and 1 mL of an ethanol co-solvent were added, and the mixture was stirred at 40° C. for 1 h. Then the heating was stopped, and the mixture was continuously stirred for 3 h at room temperature and placed in a refrigerator at 4° C. overnight. The solution described above was filtered after 12 h, and the filtrate was freeze-dried for 12 h to give a white solid powder of diethylenetriamine-β-cyclodextrin/ethinylestradiol complex.

2. Study of Inclusion Capacity of Different Host Molecules

In order to compare different inclusion capacities of various β-cyclodextrin derivatives, various clathrates with the same mass were respectively dispersed into 1 mL of a 65% methanol solution, and the quantity of ethinylestradiol contained in the complex with the same mass and a standard curve of ethinylestradiol were measured by adopting high performance liquid chromatography. The chromatography column was a C18 silica gel column, the mobile phase was a 65% methanol aqueous solution, the column temperature was 20° C., and the detection wavelength was 280 nm.

3. Structural Characterization

1) FT-IR analysis: The infrared spectrograms of the ethinylestradiol, the diethylenetriamine-β-cyclodextrin, the physical mixture of the ethinylestradiol and the diethylenetriamine-β-cyclodextrin, and the diethylenetriamine-β-cyclodextrin/ethinylestradiol complex were detected. Bruker Vertex 70, Bruker Corporation, Germany. Test conditions: The scanning range was 4000-400 $cm^{-1}$, the resolution was 4.000 $cm^{-1}$, the number of scanning was 128 times, and the attenuated total reflection technology was used for detection.

2) $^1$H NMR analysis: The changes of the microenvironment around protons of the ethinylestradiol, the diethylenetriamine-β-cyclodextrin, and the diethylenetriamine-β-cyclodextrin/ethinylestradiol complex were obtained via hydrogen nuclear magnetic resonance analysis. Nuclear magnetic hydrogen spectrum ($^1$H-NMR): AVANCE III 400 MHz, Bruker Corporation, Germany. Test conditions: The solvent was $d^6$-DMSO, and the number of scanning was 16 times.

3) Electron microscope scanning: The surface appearance and the components of the powder were detected via a scanning electron microscope.

Instrument model: Jeol JSM-6100. The multiple was 500 times.

4. Calculation of Inclusion Constant of Diethylenetriamine-β-Cyclodextrin

The inclusion constant of the diethylenetriamine-β-cyclodextrin was determined using high performance liquid chromatography to draw a phase solubility diagram.

The chromatography column was a C18 silica gel column, the mobile phase was a 65% methanol aqueous solution, the column temperature was 20° C., and the detection wavelength was 280 nm.

5. Detection of Affinity of Cyclodextrin Derivative and Rigid Ethinylestradiol

Data such as affinity, relative deviation and the like were analyzed via simulating different complex systems formed by different cyclodextrins and ethinylestradiol by using molecular dynamics simulation software GROMACS.

6. Detection of Drug Release Profile

In order to investigate the difference of the release capacities of the diethylenetriamine-β-cyclodextrin/ethinylestradiol and pure ethinylestradiol in blood, the drug release capacities of the diethylenetriamine-β-cyclodextrin/ethinylestradiol and the pure ethinylestradiol in a simulated blood environment were detected, and a drug release curve was drawn. The procedures were as follows:

In phosphate buffer (pH=7.4) in vitro simulated blood environment, the difference between the release capacity of the diethylenetriamine-β-cyclodextrin/ethinylestradiol and the pure ethinylestradiol in blood was investigated, and samples were taken at 1, 2, 4, 8, 10, 12, 14, 16, 18, 20, 24, 36, 60, 85, 110, 135, 160, 180, 210, 230, and 250 h. The absorbance was measured using a spectrophotometer model 721.

7. Solubility Detection of Diethylenetriamine-β-Cyclodextrin Including Sterol Hormone A diethylenetriamine-β-cyclodextrin/progesterone complex was prepared according to the method described in 1, and the solubility of the diethylenetriamine-β-cyclodextrin/progesterone was determined using high performance liquid chromatography.

Mobile phase: methanol:water (70:30 v/v)
Flow rate: 0.9 mL min-1
Sample injection volume: 20 μL
Column temperature: 30° C.
Detection wavelength: 241 nm
Instrument: Agilent 1290 Infinity II
Chromatographic column: Supersil ODS2 5 μm, 4.6 mm×250 mm III. Experimental Results The inclusion capacities of the different host molecules are shown in FIG. 1, and all sample solutions have similar absorption peaks and the same retention time, the retention time being 10.4 min (la), which is the same as pure ethinylestradiol, indicating that ethinylestradiol is present in the various clathrates. However, the area of each absorption peak is different. It can be seen that the contents of ethinylestradiol in these clathrates with the same mass are different, indicating that different β-cyclodextrin derivatives have different inclusion capacities for ethinylestradiol. By comparing the absorption peak areas, the chromatographic peak area of diethylenetriamine-β-cyclodextrin/ethinylestradiol is found to be the largest (1c). Further determining the amount of included ethinylestradiol, a standard curve (1b) of ethinylestradiol concentration and chromatographic peak area is drawn, wherein a linear equation is: $y=9.5547x+2.26$ ($R^2=0.9987$). As shown in FIG. 1*d*, in the clathrate solutions with the same mass concentration, the maximum solubility of the ethinylestradiol included in the diethylenetriamine-β-cyclodextrin/ethinylestradiol is 496 mg/L. By comparing the ethinylestradiol concentrations in the ethylenediamine-β-cyclodextrin/ethinylestradiol and the diethylenetriamine-β-cyclodextrin/ethinylestradiol, it can be seen that a modest increase in the length of an amine chain can increase the inclusion degree of ethinylestradiol, indicating that a modest increase in the length of an amine chain can increase the number of binding sites. However, as the length of the amine chain is further increased, the inclusion amount of the ethinylestradiol is reduced along with the increase of the mass of the β-cyclodextrin derivative, which shows that the increasing length of the amine chain cannot provide more useful binding sites, but the mass ratio of the inclusion amount of the ethinylestradiol is reduced. Compared with the common hydroxypropyl-β-cyclodextrin/ethinylestradiol, ethinylestradiol coated by the diethylenetriamine-β-cyclodextrin/ethinylestradiol has higher quality, which shows that the host and the guest of the diethylenetriamine-β-cyclodextrin/ethinylestradiol have higher affinity and stronger interaction force, and the solubilizing capacity of the diethylenetriamine-β-cyclodextrin is stronger than that of the common hydroxypropyl-β-cyclodextrin.

Figure 2:
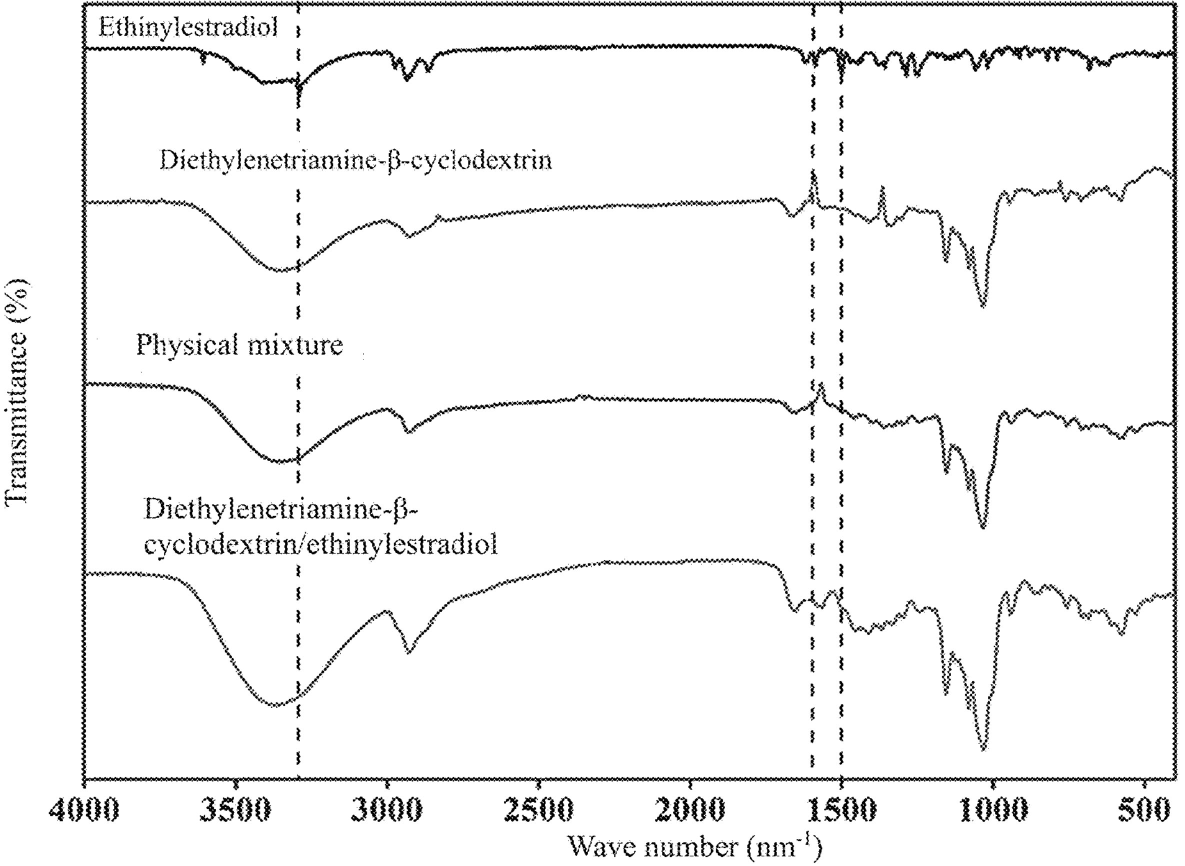
FIG. 2 is an infrared spectrogram of diethylenetriamine-β-cyclodextrin/ethinylestradiol.

The infrared spectrum result is shown in FIG. 2, the diethylenetriamine-β-cyclodextrin has significant absorption between 3000 $cm^{-1}$ to 3600 $cm^{-1}$, which belongs to the O—H and N—H stretching, and the absorption band at 2925 $cm^{-1}$ belongs to the C—H stretching. A carbon-hydrogen stretching peak of an alkynyl group appears at 3293 $cm^{-1}$ in the infrared spectrogram of the ethinylestradiol, and the peak does not appear in the infrared spectrogram of the diethylenetriamine-β-cyclodextrin/ethinylestradiol, indicating that a hydrogen bonding interaction force appears between the diethylenetriamine-β-cyclodextrin and the ethinylestradiol, which reduces the dipole moment of the alkynyl group. By comparing the spectra of the ethinylestradiol, the diethylenetriamine-β-cyclodextrin, the physical mixture and the diethylenetriamine-β-cyclodextrin/ethinylestradiol clathrate, the stretching peaks of phenyl C—C bonds between 1500 $cm^{-1}$ and 1612 $cm^{-1}$ are found to be significantly different. After the diethylenetriamine-β-cyclodextrin/ethinylestradiol is formed, an absorption peak at 1579 $cm^{-1}$ indicates that phenyl exists in the diethylenetriamine-β-cyclodextrin/ethinylestradiol. The physical mixture and the diethylenetriamine-β-cyclodextrin/ethinylestradiol clathrate have different infrared absorption peak shapes between 1500 $cm^{-1}$ and 1612 $cm^{-1}$, which indicates that the ethinylestradiol is embedded into the cavity of the diethylenetriamine- β-cyclodextrin/ethinylestradiol via conjugation. It is indicated that the ethinylestradiol interacts with the diethylenetriamine-β-cyclodextrin to form a complex rather than forming a simple mixture via adsorption.

Figure 3:
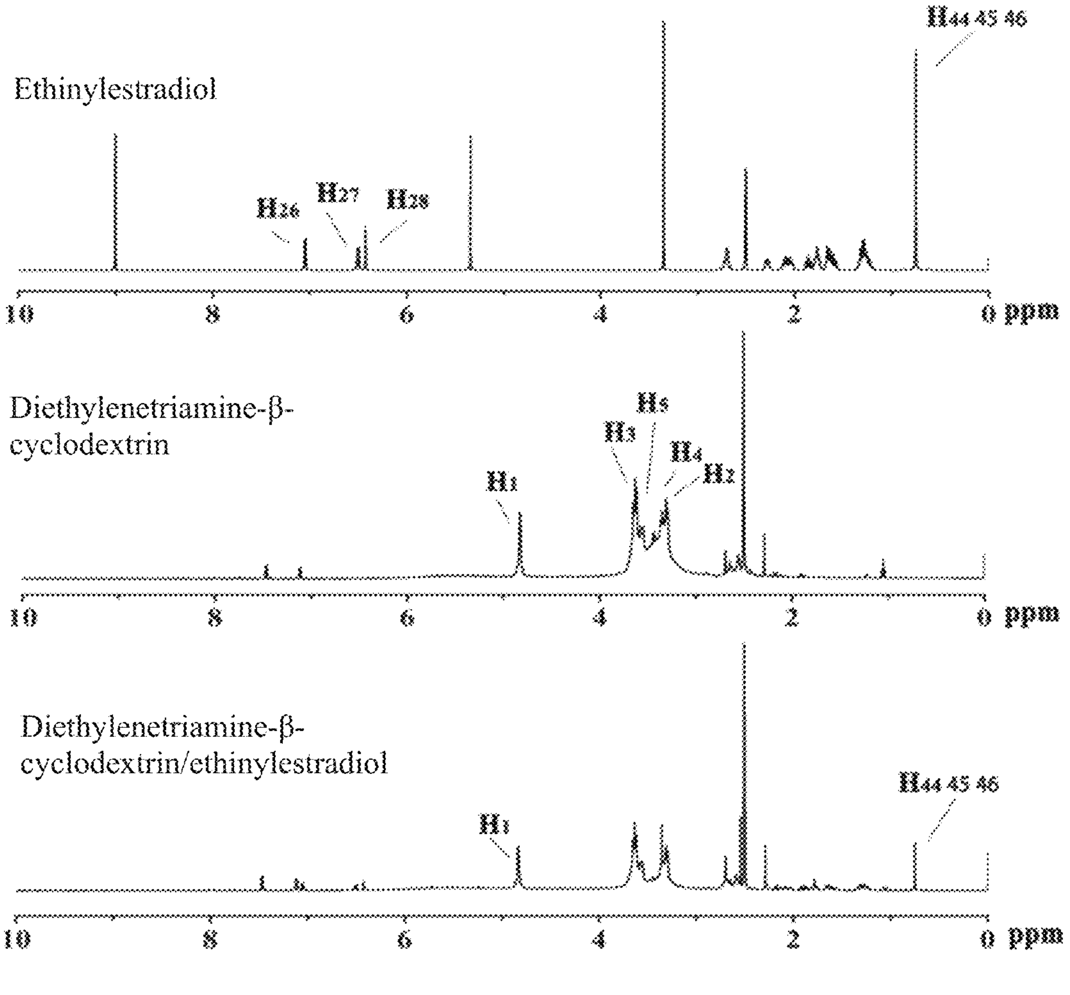
FIG. 3 is a hydrogen nuclear magnetic resonance spectrum of diethylenetriamine-β-cyclodextrin/ethinylestradiol.

The nuclear magnetic resonance spectrum results are shown in FIG. 3. The δ value of $H_{44\ 45\ 46}$ in the ethinylestradiol is 0.737 ppm, whereas the δ value is shifted to low field in the diethylenetriamine-β-cyclodextrin/ethinylestradiol (the δ value increases, Δδ=0.023 ppm), and the δ value of Hi is 4.819 ppm in the diethylenetriamine-β-cyclodextrin, and 4.835 ppm in the diethylenetriamine-β-cyclodextrin/ethinylestradiol, indicating that the van der Waals interaction force between methyl in the ethinylestradiol and the diethylenetriamine-β-cyclodextrin decreases the shielding effect. The protons of $H_3$ and $H_5$ in the diethylenetriamine-β-cyclodextrin have δ values of 3.634 ppm and 3.565 ppm respectively, and the δ values are shifted to high field after the clathrate is formed, which shows that the ethinylestradiol enters the hydrophobic cavity via hydrophobic interaction force, the density of the electron cloud in the cavity is increased due to electrostatic interaction and conjugation effect, and the shielding effect is enhanced. It is indicated that the ethinylestradiol enters the hydrophobic cavity of the diethylenetriamine-β-cyclodextrin via van der Waals interaction, hydrogen bonding interaction and conjugation to form a water-soluble clathrate, which is consistent with the result of the infrared spectrogram.

Figure 4:
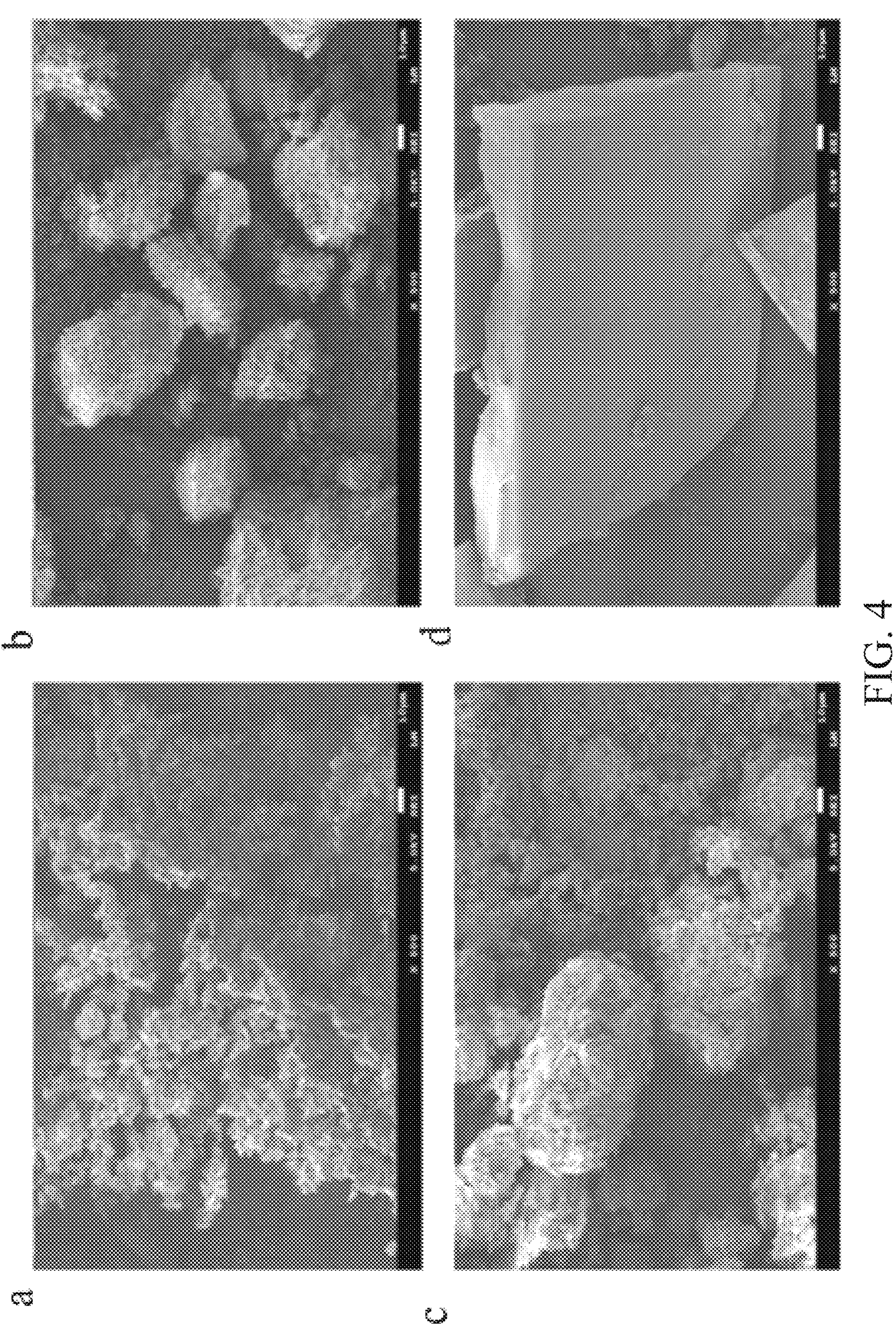
FIG. 4 is a scanning electron micrograph of different substances, wherein 4*a* is a scanning electron micrograph of ethinylestradiol, 4*b* is a scanning electron micrograph of diethylenetriamine-β-cyclodextrin, 4*c* is a scanning electron micrograph of a physical mixture, and 4*d* is a scanning electron micrograph of diethylenetriamine-β-cyclodextrin/ethinylestradiol.

The electron microscope scanning results are shown in FIG. 4. An irregular crystal structure appears in the scanning electron micrograph of the ethinylestradiol, a porous structure with a rough surface appears in the scanning electron micrograph of the diethylenetriamine-β-cyclodextrin shown in 4*b*, and a plurality of crystals with a structure similar to that of the pure diethylenetriamine-β-cyclodextrin can be observed in the scanning electron micrograph (4*c*) of the physical mixture of the ethinylestradiol and the diethylenetriamine-β-cyclodextrin. A comparison of the transmission electron micrographs of the physical mixture and the diethylenetriamine-β-cyclodextrin/ethinylestradiol clathrate (4*d*) shows that the diethylenetriamine-β-cyclodextrin/ethinylestradiol clathrate presents a uniform and compact plate-shaped crystal structure, which is significantly different from the structure of the physical mixture, illustrates the change of the physical properties of the crystal, and proves the formation of the clathrate.

Figures 5, 6:
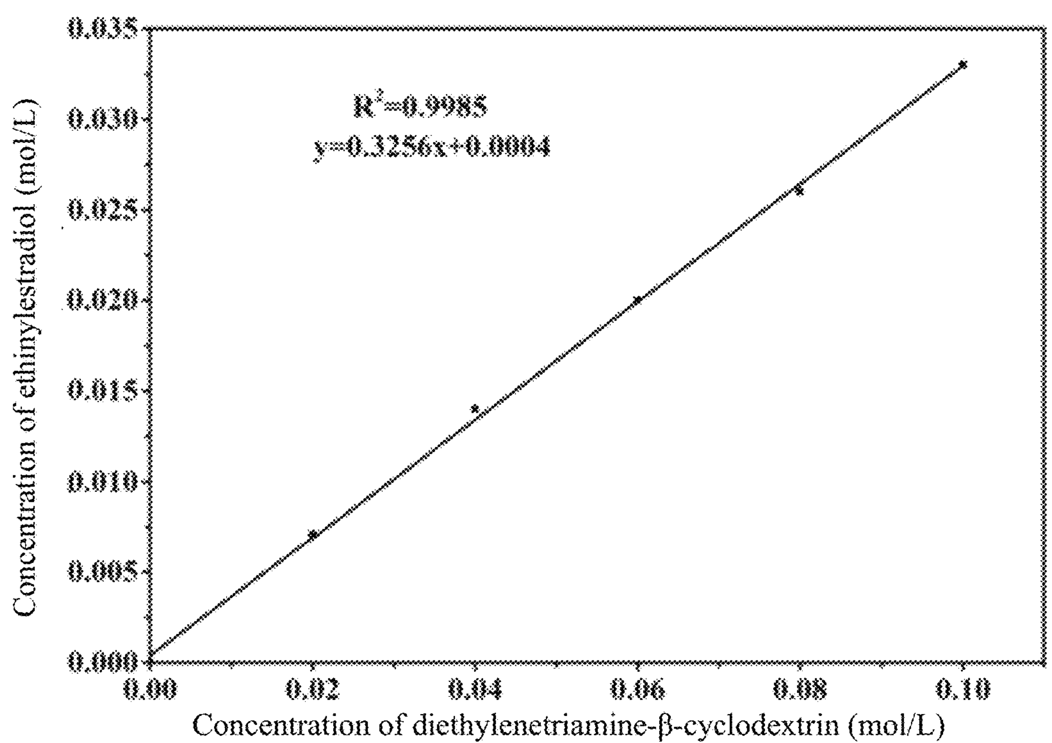
FIG. 5 is a phase solubility diagram of a diethylenetriamine-β-cyclodextrin/ethinylestradiol system.
FIG. 6 is a molecular-simulation 3D model of different substances, wherein 6*a* is β-cyclodextrin/ethinylestradiol, 6*b* is ethylenediamine-β-cyclodextrin/ethinylestradiol, 6*c* is diethylenetriamine-β-cyclodextrin/ethinylestradiol, 6*e* is triethylenetetramine-β-cyclodextrin/ethinylestradiol, 6*f* is tetraethylenepentamine-β-cyclodextrin/ethinylestradiol, and 6g is hydroxypropyl-β-cyclodextrin/ethinylestradiol.

The detection result of the phase solubility is shown in FIG. 5. The solubility of the ethinylestradiol linearly increases with the increase of the concentration of the diethylenetriamine-β-cyclodextrin, which is of the same type as a typical AL model, indicating that a soluble clathrate having a stoichiometric ratio of 1:1 is formed between the diethylenetriamine-β-cyclodextrin and the ethinylestradiol. The stability constant (K) of the diethylenetriamine-β-cyclodextrin/ethinylestradiol at 293 K is 1206.9 L/mol, and the calculation formula is as follows:

$$K = \frac{\text{slope}}{\text{intercept}\,(1 - \text{slope})}$$

The spontaneity of the formation of the clathrate in the solution can be determined by calculating the change of Gibbs free energy (ΔG) in the process of inclusion of the ethinylestradiol and the diethylenetriamine-β-cyclodextrin, and the calculation formula is as follows:

$$\Delta G = -RT \ln K$$

The calculated value of ΔG is −17.29 KJ/mol. A negative value of ΔG indicates that the ethinylestradiol spontaneously enters the hydrophobic cavity of the diethylenetriamine-β-cyclodextrin, indicating that the two molecules have high affinity. The research result of phase solubility shows that the ethinylestradiol and the diethylenetriamine-β-cyclodextrin are mutually combined via a host-guest encapsulation cooperation, so that a stable diethylenetriamine-β-cyclodextrin/ethinylestradiol encapsulation complex is formed to a great extent, and an ethinylestradiol self-assembly solubilization system is established successfully.

The simulation results of binding energy and interaction force are shown in Table 1 to Table 6. Compared with the β-cyclodextrin/ethinylestradiol (−12.14 KJ), the ethylenediamine-β-cyclodextrin/ethinylestradiol (−24.70 KJ), triethylenetetramine-β-cyclodextrin/ethinylestradiol (−20.93 KJ), tetraethylenepentamine-β-cyclodextrin/ethinylestradiol (−14.23 KJ), and hydroxypropyl-β-cyclodextrin/ethinylestradiol (−19.67 KJ), the affinity for forming the diethylenetriamine-β-cyclodextrin/ethinylestradiol is the highest, and can reach −26.37 KJ.

TABLE 1

β-Cyclodextrin/ethinylestradiol molecular simulation docking data

| Type of docking | Affinity (kcal mol$^{-1}$) | Relative deviation of docking distance | Relative deviation from optimal docking |
|---|---|---|---|
| 1 | −2.9 | 0 | 0 |
| 2 | −2.6 | 1.831 | 3.697 |
| 3 | −2.5 | 2.573 | 4.632 |
| 4 | −2.5 | 2.733 | 6.670 |
| 5 | −2.5 | 1.817 | 2.581 |
| 6 | −2.4 | 2.363 | 4.256 |
| 7 | −2.3 | 2.747 | 6.905 |
| 8 | −2.3 | 4.945 | 6.599 |
| 9 | −2.3 | 3.527 | 5.368 |

TABLE 2

Ethylenediamine-β-cyclodextrin/ethinylestradiol molecular simulation docking data

| Type of docking | Affinity (kcal mol$^{-1}$) | Relative deviation of docking distance | Relative deviation from optimal docking |
|---|---|---|---|
| 1 | −5.9 | 0 | 0 |
| 2 | −5.6 | 1.866 | 3.538 |
| 3 | −5.5 | 3.540 | 6.293 |
| 4 | −4.9 | 3.247 | 7.173 |
| 5 | −4.6 | 3.367 | 7.314 |
| 6 | −4.6 | 3.766 | 6.686 |
| 7 | −4.4 | 2.783 | 7.628 |
| 8 | −4.3 | 4.550 | 7.634 |
| 9 | −3.6 | 5.374 | 7.862 |

TABLE 3

Diethylenetriamine-β-cyclodextrin/ethinylestradiol molecular simulation docking data

| Type of docking | Affinity (kcal mol$^{-1}$) | Relative deviation of docking distance | Relative deviation from optimal docking |
|---|---|---|---|
| 1 | −6.2 | 0 | 0 |
| 2 | −6.2 | 2.692 | 4.139 |
| 3 | −6.1 | 1.847 | 3.083 |

TABLE 3-continued

| Diethylenetriamine-β-cyclodextrin/ethinylestradiol molecular simulation docking data | | | |
|---|---|---|---|
| Type of docking | Affinity (kcal $mol^{-1}$) | Relative deviation of docking distance | Relative deviation from optimal docking |
| 4 | −6.1 | 1.384 | 6.901 |
| 5 | −6.0 | 1.375 | 1.506 |
| 6 | −6.0 | 2.730 | 6.227 |
| 7 | −5.9 | 1.687 | 1.949 |
| 8 | −5.9 | 2.520 | 3.492 |
| 9 | −5.9 | 2.562 | 6.488 |

TABLE 4

| Triethylenetetramine-β-cyclodextrin/ethinylestradiol molecular simulation docking data | | | |
|---|---|---|---|
| Type of docking | Affinity (kcal $mol^{-1}$) | Relative deviation of docking distance | Relative deviation from optimal docking |
| 1 | −5.0 | 0 | 0 |
| 2 | −4.6 | 1.609 | 2.772 |
| 3 | −4.4 | 4.178 | 6.865 |
| 4 | −4.2 | 3.906 | 4.919 |
| 5 | −3.9 | 4.574 | 6.339 |
| 6 | −3.4 | 2.306 | 3.179 |
| 7 | −3.1 | 5.020 | 5.838 |
| 8 | −3.0 | 11.412 | 13.575 |
| 9 | −2.9 | 10.061 | 12.071 |

TABLE 5

| Tetraethylenepentamine-β-cyclodextrin/ethinylestradiol molecular simulation docking data | | | |
|---|---|---|---|
| Type of docking | Affinity (kcal $mol^{-1}$) | Relative deviation of docking distance | Relative deviation from optimal docking |
| 1 | −3.4 | 0 | 0 |
| 2 | −3.1 | 2.490 | 3.709 |
| 3 | −2.5 | 3.532 | 5.354 |
| 4 | −2.2 | 7.624 | 9.866 |
| 5 | −2.2 | 8.773 | 11.376 |
| 6 | −2.1 | 5.359 | 7.597 |
| 7 | −2.1 | 7.328 | 9.486 |
| 8 | −2.0 | 7.768 | 10.350 |
| 9 | −2.0 | 7.500 | 10.522 |

TABLE 6

| Hydroxypropyl-β-cyclodextrin/ethinylestradiol molecular simulation docking data | | | |
|---|---|---|---|
| Type of docking | Affinity (kcal $mol^{-1}$) | Relative deviation of docking distance | Relative deviation from optimal docking |
| 1 | −4.7 | 0 | 0 |
| 2 | −4.0 | 1.938 | 2.347 |
| 3 | −4.0 | 1.812 | 6.832 |
| 4 | −3.8 | 3.975 | 7.203 |
| 5 | −3.7 | 3.174 | 5.892 |
| 6 | −3.7 | 2.496 | 7.134 |
| 7 | −3.7 | 1.365 | 2.770 |
| 8 | −3.6 | 2.269 | 7.327 |
| 9 | −3.6 | 2.708 | 3.772 |

The structural forms of different host molecules docked with the ethinylestradiol under the minimum bond energy are shown in FIG. 6. Hydrogen bonding exists between the ethinylestradiol and the β-cyclodextrin/ethinylestradiol, the ethylenediamine-β-cyclodextrin/ethinylestradiol, the triethylenetetramine-β-cyclodextrin/ethinylestradiol, and the hydroxypropyl-β-cyclodextrin/ethinylestradiol, π bonding exists between the ethinylestradiol and the diethylenetriamine-β-cyclodextrin/ethinylestradiol and the tetraethylenepentamine-β-cyclodextrin/ethinylestradiol, and the length of the π bond in the diethylenetriamine-β-cyclodextrin/ethinylestradiol is shorter than the π bond in the tetraethylenepentamine-β-cyclodextrin/ethinylestradiol. The diethylenetriamine-β-cyclodextrin/ethinylestradiol has a more stable structure by comparing the type and the length of bonds and combining the size of affinity. In addition, various interaction forces such as hydrophobic interaction force, electrostatic interaction force, van der Waals interaction force and the like exist between the hydrophobic alkyl of the diethylenetriamine-β-cyclodextrin and the ethinylestradiol, so that docking molecules are more stable, the ethinylestradiol is not easy to separate from the hydrophobic cavity of the diethylenetriamine-β-cyclodextrin, and the side chain of the diethylenetriamine-β-cyclodextrin limits the movement of the ethinylestradiol in the cavity, so that the clathrate is more stable. The stability and the water solubility of ethinylestradiol are greatly improved by taking diethylenetriamine-β-cyclodextrin as a host molecule.

Figure 7:
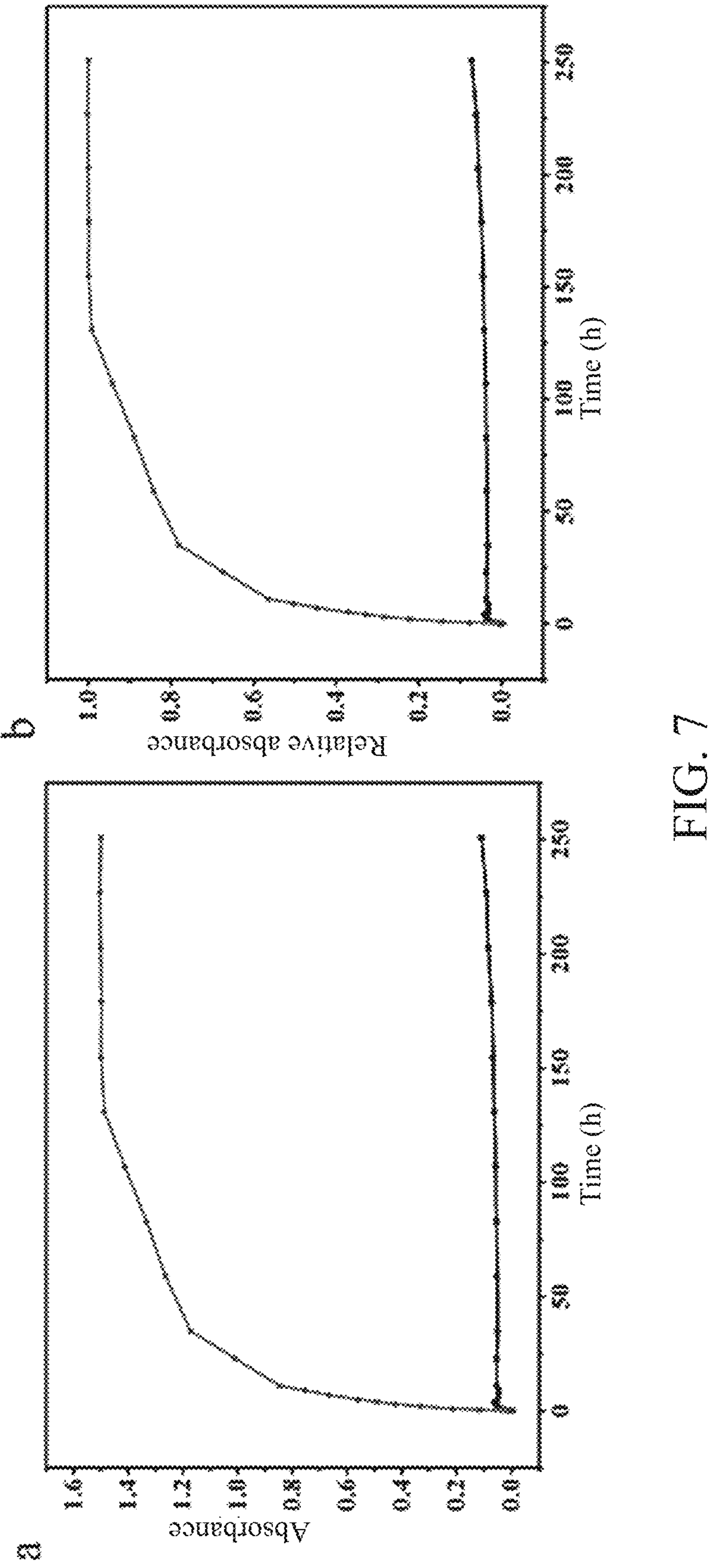
FIG. 7 is a drug release profile, wherein 7*a* is the absorbance over time, and 7*b* is the relative absorbance over time.

The release capacities of the diethylenetriamine-β-cyclodextrin/ethinylestradiol and the pure ethinylestradiol in blood are shown in FIG. 7, wherein the black represents the ethinylestradiol, and the red represents the diethylenetriamine-β-cyclodextrin/ethinylestradiol. The diethylenetriamine-β-cyclodextrin/ethinylestradiol shows superior dissolution and release capacity compared to the pure ethinylestradiol. When the release experiment is started, the diethylenetriamine-β-cyclodextrin/ethinylestradiol is released quickly, and the pure ethinylestradiol is almost not released. One week later, the diethylenetriamine-β-cyclodextrin/ethinylestradiol reaches release balance, and more ethinylestradiol can be released. After being placed for a long time, the diethylenetriamine-β-cyclodextrin/ethinylestradiol solution still keeps stable and uniform without precipitation, indicating that the diethylenetriamine-β-cyclodextrin/ethinylestradiol can be dissolved in a blood environment and keep stable for a long time. While the pure ethinylestradiol is almost not released from the dialysis bag, and a large amount of insoluble ethinylestradiol is found in the dialysis bag. When the release balance is reached, the release amount of the diethylenetriamine-β-cyclodextrin/ethinylestradiol is about 100 times that of the pure ethinylestradiol, which corresponds to the solubility result. It is proved that diethylenetriamine-β-cyclodextrin/ethinylestradiol has good stability and solubility in blood, can greatly improve the utilization rate of ethinylestradiol, and provides new possibility for the appearance of homogeneous ethinylestradiol injection.

Figure 8:
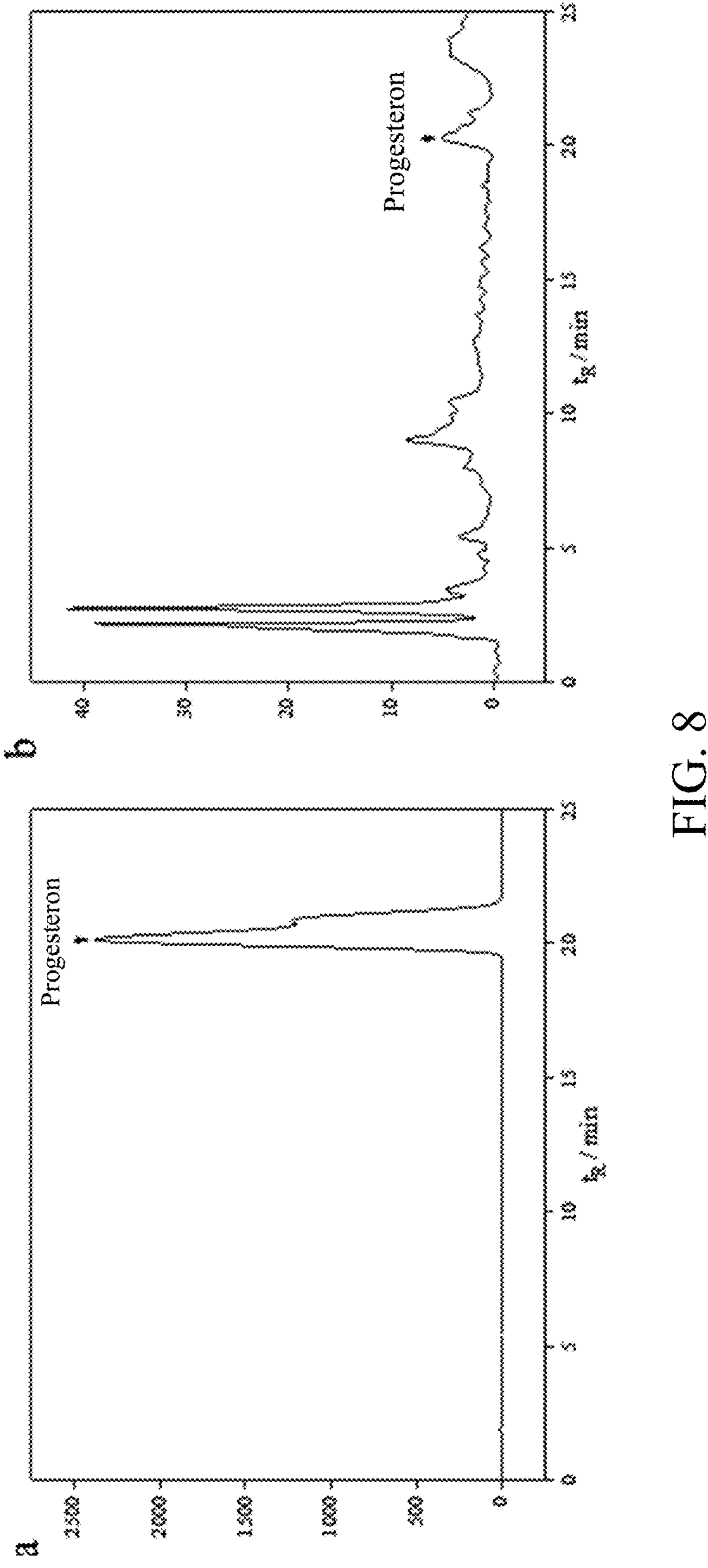
FIG. 8 is a liquid chromatogram of progesterone, wherein 8*a* is a liquid chromatogram of progesterone standard substance, and 8*b* is a liquid chromatogram of the diethylenetriamine cyclodextrin/progesterone complex.

The result of the quantitative determination of the diethylenetriamine-β-cyclodextrin/progesterone is shown in FIG. 8. The diethylenetriamine-β-cyclodextrin substantially has no solubilizing effect on progesterone which is also sterol hormone and has a similar structure.

Finally, it should be understood that the examples described herein are merely illustrative of the principles of examples of the present application. Other variations are also possible within the scope of the present application. Thus, by way of example, and not limitation, alternative configurations of examples of the present application may be considered consistent with the teachings of the present application. Accordingly, the examples of the present application are not limited to the examples explicitly introduced and described in the present application.

The invention claimed is:

1. A pharmaceutical composition, comprising ethinylestradiol and cyclodextrin, wherein the ethinylestradiol and the cyclodextrin interact to form a clathrate, and the cyclodextrin is β-cyclodextrin or a derivative thereof, wherein β-cyclodextrin is selected from ethylenediamine-β-cyclodextrin, diethylenetriamine-β-cyclodextrin, triethylenetetramine-β-cyclodextrin, tetraethylenepentamine-β-cyclodextrin, and hydroxypropyl-β-cyclodextrin.

2. The pharmaceutical composition according to claim 1, wherein the β-cyclodextrin derivative is diethylenetriamine-β-cyclodextrin.

3. The pharmaceutical composition according to claim 1, wherein the cyclodextrin and the ethinylestradiol have a stoichiometric ratio of 1:1.

4. The pharmaceutical composition according to claim 1, wherein a preparation method for the clathrate is as follows:

dissolving the cyclodextrin in deionized water, adding the ethinylestradiol and a co-solvent, heating and stirring the mixture; then continuously stirring the mixture at room temperature and keeping the mixture overnight at low temperature; filtering the mixture, and drying to give a white solid powder.

5. The pharmaceutical composition according to claim 4, wherein the co-solvent is ethanol.

6. The pharmaceutical composition according to claim 4, wherein the drying is freeze drying.

7. The pharmaceutical composition according to claim 2, wherein a preparation method for diethylenetriamine-β-cyclodextrin comprises:

1) dissolving β-cyclodextrin in a sodium hydroxide solution to give an alkaline β-cyclodextrin solution;

2) dissolving toluenesulfonyl chloride in acetonitrile, adding the mixture to the alkaline β-cyclodextrin solution described above, adjusting the pH to give a suspension, obtaining a precipitate at low temperature, and drying to give 6-p-toluenesulfonyl-β-cyclodextrin; and 3) dissolving the 6-p-toluenesulfonyl-β-cyclodextrin in N-methylpyrrolidone, heating, adding potassium iodide and diethylenetriamine, stirring the mixture at high temperature under nitrogen atmosphere, then cooling to room temperature, collecting a precipitate, and drying to give the diethylenetriamine-β-cyclodextrin.

8. The pharmaceutical composition according to claim 7, wherein the pH is adjusted to 5-7 with hydrochloric acid in Step 2).

9. The pharmaceutical composition according to claim 7, wherein the suspension in Step 2) is at 4° C. overnight to give a precipitate.

10. The pharmaceutical composition according to claim 7, wherein the precipitate in Step 2) is washed with ethanol.

11. The pharmaceutical composition according to claim 7, wherein the drying is at 50° C. to give 6-p-toluenesulfonyl-β-cyclodextrin in Step 2).

12. The pharmaceutical composition according to claim 7, wherein the mixture is stirred at 70° C. under nitrogen atmosphere in Step 3).

13. The pharmaceutical composition according to claim 7, wherein the precipitate is collected using suction filtration in Step 3).

14. The pharmaceutical composition according to claim 7, wherein the precipitate in Step 3) is dried under vacuum.

15. The pharmaceutical composition according to claim 1, further comprising a pharmaceutically acceptable carrier.

16. A method for preparing the pharmaceutical composition according to claim 1, comprising: dissolving the cyclodextrin in deionized water, adding the ethinylestradiol and a co-solvent, heating and stirring the mixture; then continuously stirring the mixture at room temperature and keeping the mixture overnight at low temperature; filtering the mixture, and drying to give a white solid powder.

17. A method for increasing the solubility of ethinylestradiol and improving the release performance of the ethinylestradiol, wherein the pharmaceutical composition according to claim 1 is prepared.

18. A method for contraception or for treating a gynecological disease, comprising administering to a subject in need thereof an effective amount of the pharmaceutical composition according to claim 1.

19. The method according to claim 18, wherein the subject is a mammal.

20. The method according to claim 19, wherein the mammal includes a human, a non-human primate, a rabbit, a sheep, a rat, a dog, a cat, a pig, or a mouse.

* * * * *